(12) United States Patent
Sartor et al.

(10) Patent No.: US 8,608,739 B2
(45) Date of Patent: Dec. 17, 2013

(54) ELECTROSURGICAL DEVICES, SYSTEMS AND METHODS OF USING THE SAME

(75) Inventors: Joe D. Sartor, Longmont, CO (US); David N. Heard, Boulder, CO (US)

(73) Assignee: Covidien LP, Mansfield, MA (US)

( * ) Notice: Subject to any disclaimer, the term of this patent is extended or adjusted under 35 U.S.C. 154(b) by 992 days.

(21) Appl. No.: 12/177,327

(22) Filed: Jul. 22, 2008

(65) Prior Publication Data
US 2010/0023007 A1    Jan. 28, 2010

(51) Int. Cl.
*A61B 18/18* (2006.01)

(52) U.S. Cl.
USPC .................................. 606/49; 606/41; 606/45

(58) Field of Classification Search
USPC ............ 606/49, 41, 45, 51, 48; 607/100, 116; 604/9
See application file for complete search history.

(56) References Cited

U.S. PATENT DOCUMENTS

| | | | |
|---|---|---|---|
| 2,031,682 A | 2/1936 | Frederick et al. |
| 4,074,718 A | 2/1978 | Morrison, Jr. et al. |
| 4,375,220 A | 3/1983 | Matvias |
| 4,411,266 A | 10/1983 | Cosman |
| 4,565,200 A | 1/1986 | Cosman |
| 4,576,177 A | 3/1986 | Webster, Jr. |
| 4,608,977 A | 9/1986 | Brown |
| 4,662,383 A | 5/1987 | Sogawa et al. |
| 4,739,759 A | 4/1988 | Rexwroth et al. |
| 4,832,024 A | 5/1989 | Boussignac et al. |
| 4,880,719 A | 11/1989 | Murofushi et al. |
| 4,961,435 A | 10/1990 | Kitagawa et al. |
| 4,966,597 A | 10/1990 | Cosman |
| 4,993,430 A | 2/1991 | Shimoyama et al. |
| 5,029,588 A | 7/1991 | Yock et al. |
| 5,103,804 A | 4/1992 | Abele et al. |
| 5,225,741 A | 7/1993 | Auld et al. |
| 5,230,623 A | 7/1993 | Guthrie et al. |
| 5,233,515 A | 8/1993 | Cosman |
| 5,246,438 A | 9/1993 | Langberg |
| 5,267,994 A | 12/1993 | Gentelia et al. |
| 5,281,213 A | 1/1994 | Milder et al. |

(Continued)

FOREIGN PATENT DOCUMENTS

| | | |
|---|---|---|
| DE | 2407559 | 2/1974 |
| DE | 10224154 | 12/2003 |

(Continued)

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.

(Continued)

*Primary Examiner* — Nicholas Lucchesi
*Assistant Examiner* — Brooke Matney

(57) ABSTRACT

According to an aspect of the present disclosure, a desiccation device for operation on a target tissue is provided. The device includes a handle; a shaft extending distally from the handle, wherein the shaft defines a lumen therethrough; and a head having a loop configuration supported on a distal end of the shaft, the head being hollow and defining a lumen therethrough, said lumen being in fluid communication with the lumen of the shaft. At least a portion of the cutting head is electrically connected to a source of electrosurgical energy. A fluid is circulatable through the lumen of the shaft and the head.

11 Claims, 8 Drawing Sheets

(56) References Cited

U.S. PATENT DOCUMENTS

| | | |
|---|---|---|
| 5,323,778 A | 6/1994 | Kandarpa et al. |
| 5,330,470 A | 7/1994 | Hagen |
| 5,330,518 A | 7/1994 | Nielson et al. |
| 5,334,193 A | 8/1994 | Nardella |
| 5,342,357 A | 8/1994 | Nardella |
| 5,348,554 A | 9/1994 | Imran et al. |
| 5,370,675 A | 12/1994 | Edwards et al. |
| 5,383,876 A | 1/1995 | Nardella |
| 5,383,917 A | 1/1995 | Desai et al. |
| 5,385,148 A | 1/1995 | Lesh et al. |
| 5,403,311 A | 4/1995 | Abele et al. |
| 5,409,000 A | 4/1995 | Imran |
| 5,409,006 A | 4/1995 | Buchholtz et al. |
| 5,417,686 A | 5/1995 | Peterson et al. |
| 5,433,739 A | 7/1995 | Sluijter et al. |
| 5,437,662 A | 8/1995 | Nardella |
| 5,458,597 A | 10/1995 | Edwards et al. |
| 5,462,521 A | 10/1995 | Brucker et al. |
| 5,472,441 A | 12/1995 | Edwards et al. |
| 5,486,183 A | 1/1996 | Middleman et al. |
| 5,490,850 A | 2/1996 | Ellman et al. |
| 5,500,012 A | 3/1996 | Brucker et al. |
| 5,520,684 A | 5/1996 | Imran |
| 5,536,267 A | 7/1996 | Edwards et al. |
| 5,571,147 A | 11/1996 | Sluijter et al. |
| 5,588,432 A | 12/1996 | Crowley |
| 5,599,345 A | 2/1997 | Edwards et al. |
| 5,643,197 A | 7/1997 | Brucker et al. |
| 5,647,871 A | 7/1997 | Levine et al. |
| 5,662,111 A | 9/1997 | Cosman |
| 5,688,267 A | 11/1997 | Panescu et al. |
| 5,735,847 A | 4/1998 | Gough et al. |
| 5,775,338 A | 7/1998 | Hastings |
| 5,788,694 A | 8/1998 | Vancaillie |
| 5,792,146 A | 8/1998 | Cosman |
| 5,848,967 A | 12/1998 | Cosman |
| 5,849,011 A | 12/1998 | Jones et al. |
| 5,868,740 A | 2/1999 | LeVeen et al. |
| 5,904,690 A | 5/1999 | Middleman et al. |
| 5,921,982 A | 7/1999 | Lesh et al. |
| 5,951,546 A | 9/1999 | Lorentzen |
| 6,001,093 A | 12/1999 | Swanson et al. |
| 6,006,126 A | 12/1999 | Cosman |
| 6,013,076 A | 1/2000 | Goble |
| 6,024,740 A | 2/2000 | Lesh et al. |
| 6,053,912 A | 4/2000 | Panescu et al. |
| 6,053,925 A | 4/2000 | Barnhart |
| 6,059,780 A | 5/2000 | Gough et al. |
| 6,061,551 A | 5/2000 | Sorrells et al. |
| 6,074,389 A | 6/2000 | Levine et al. |
| 6,080,149 A | 6/2000 | Huang et al. |
| 6,106,524 A | 8/2000 | Eggers et al. |
| 6,117,101 A | 9/2000 | Diederich et al. |
| 6,132,426 A | 10/2000 | Kroll |
| 6,146,380 A | 11/2000 | Racz et al. |
| 6,162,216 A | 12/2000 | Guziak et al. |
| 6,203,541 B1 | 3/2001 | Keppel |
| 6,217,528 B1 | 4/2001 | Koblish et al. |
| 6,241,725 B1 | 6/2001 | Cosman |
| 6,245,064 B1 | 6/2001 | Lesh et al. |
| 6,246,912 B1 | 6/2001 | Sluijter et al. |
| 6,280,441 B1 | 8/2001 | Ryan |
| 6,287,305 B1 | 9/2001 | Heim et al. |
| 6,306,132 B1 | 10/2001 | Moorman et al. |
| 6,308,091 B1 | 10/2001 | Avitall |
| 6,337,998 B1 | 1/2002 | Behl et al. |
| 6,432,070 B1 | 8/2002 | Talish et al. |
| 6,478,793 B1 | 11/2002 | Cosman et al. |
| 6,500,172 B1 | 12/2002 | Panescu et al. |
| 6,506,189 B1 | 1/2003 | Rittman, III et al. |
| 6,517,538 B1 | 2/2003 | Jacob et al. |
| 6,530,922 B2 | 3/2003 | Cosman et al. |
| 6,575,969 B1 | 6/2003 | Rittman, III et al. |
| 6,599,288 B2 | 7/2003 | Maguire et al. |
| 6,605,085 B1 | 8/2003 | Edwards |
| 6,613,047 B2 | 9/2003 | Edwards |
| 6,652,515 B1 | 11/2003 | Maguire et al. |
| 6,685,729 B2 | 2/2004 | Gonzalez |
| 6,702,810 B2 | 3/2004 | McClurken et al. |
| 6,761,733 B2 | 7/2004 | Chobotov et al. |
| 6,997,925 B2 | 2/2006 | Maguire et al. |
| 7,063,682 B1 | 6/2006 | Whayne et al. |
| 7,137,980 B2 | 11/2006 | Buysse et al. |
| 7,156,842 B2 | 1/2007 | Sartor et al. |
| 7,179,255 B2 | 2/2007 | Lettice et al. |
| 7,186,222 B1 | 3/2007 | Callister et al. |
| 7,195,608 B2 * | 3/2007 | Burnett .............. 604/9 |
| 7,197,363 B2 | 3/2007 | Prakash et al. |
| 7,207,989 B2 | 4/2007 | Pike, Jr. et al. |
| 7,218,958 B2 | 5/2007 | Rashidi |
| 7,235,070 B2 | 6/2007 | Vanney |
| 7,235,073 B2 | 6/2007 | Levine et al. |
| 7,238,184 B2 | 7/2007 | Megerman et al. |
| 7,245,955 B2 | 7/2007 | Rashidi |
| 7,264,619 B2 | 9/2007 | Venturelli |
| 7,278,991 B2 | 10/2007 | Morris et al. |
| 7,282,049 B2 | 10/2007 | Orszulak et al. |
| 7,285,119 B2 | 10/2007 | Stewart et al. |
| 7,294,127 B2 | 11/2007 | Leung et al. |
| 7,294,143 B2 | 11/2007 | Francischelli |
| 7,302,285 B2 | 11/2007 | Fuimaono et al. |
| 7,303,558 B2 | 12/2007 | Swanson |
| 7,331,947 B2 | 2/2008 | McGuckin, Jr. et al. |
| RE40,156 E | 3/2008 | Sharps et al. |
| 7,341,586 B2 | 3/2008 | Daniel et al. |
| 7,344,533 B2 | 3/2008 | Pearson et al. |
| 7,364,578 B2 | 4/2008 | Francischelli et al. |
| 7,364,579 B2 | 4/2008 | Mulier et al. |
| 7,367,974 B2 | 5/2008 | Haemmerich et al. |
| 7,367,975 B2 | 5/2008 | Malecki et al. |
| 7,387,625 B2 | 6/2008 | Hovda et al. |
| 7,419,486 B2 | 9/2008 | Kampa |
| 7,419,487 B2 | 9/2008 | Johnson et al. |
| 7,419,488 B2 | 9/2008 | Ciarrocca et al. |
| 7,419,489 B2 | 9/2008 | Vanney et al. |
| 7,422,587 B2 | 9/2008 | Bek et al. |
| 2001/0034518 A1 | 10/2001 | Edwards et al. |
| 2002/0058933 A1 | 5/2002 | Christopherson et al. |
| 2002/0087151 A1 | 7/2002 | Mody et al. |
| 2002/0111615 A1 | 8/2002 | Cosman et al. |
| 2002/0120261 A1 | 8/2002 | Morris et al. |
| 2002/0156472 A1 | 10/2002 | Lee et al. |
| 2003/0014048 A1 | 1/2003 | Swanson |
| 2003/0018247 A1 | 1/2003 | Gonzalez |
| 2004/0002745 A1 | 1/2004 | Fleming et al. |
| 2004/0039429 A1 | 2/2004 | Daniel et al. |
| 2004/0181216 A1 | 9/2004 | Kelly et al. |
| 2004/0199161 A1 | 10/2004 | Truckai et al. |
| 2004/0254573 A1 | 12/2004 | Dycus |
| 2004/0267256 A1 | 12/2004 | Garabedian et al. |
| 2005/0010095 A1 | 1/2005 | Stewart et al. |
| 2005/0033278 A1 | 2/2005 | McClurken et al. |
| 2005/0065584 A1 | 3/2005 | Schiff et al. |
| 2005/0096681 A1 | 5/2005 | Desinger et al. |
| 2005/0107784 A1 | 5/2005 | Moses |
| 2005/0107785 A1 | 5/2005 | Dycus |
| 2005/0113824 A1 | 5/2005 | Sartor et al. |
| 2005/0119655 A1 | 6/2005 | Moses |
| 2005/0154387 A1 | 7/2005 | Moses |
| 2005/0155743 A1 | 7/2005 | Getz, Jr. et al. |
| 2005/0192564 A1 | 9/2005 | Cosman et al. |
| 2006/0009833 A1 | 1/2006 | Chobotov et al. |
| 2006/0079885 A1 | 4/2006 | Rick et al. |
| 2006/0079887 A1 | 4/2006 | Buysse |
| 2006/0111710 A1 | 5/2006 | Goble |
| 2006/0259032 A1 | 11/2006 | Nesbitt |
| 2007/0066971 A1 | 3/2007 | Podhajsky |
| 2007/0073285 A1 | 3/2007 | Peterson |
| 2007/0078453 A1 | 4/2007 | Johnson |
| 2007/0078454 A1 | 4/2007 | McPherson |
| 2007/0118110 A1 | 5/2007 | Girard et al. |
| 2007/0198006 A1 | 8/2007 | Prakash et al. |
| 2007/0208339 A1 | 9/2007 | Arts et al. |
| 2007/0219546 A1 | 9/2007 | Mody et al. |

(56) References Cited

U.S. PATENT DOCUMENTS

| | | |
|---|---|---|
| 2007/0270794 A1 | 11/2007 | Anderson et al. |
| 2007/0299435 A1 | 12/2007 | Crowe et al. |
| 2008/0021448 A1 | 1/2008 | Orszulak |
| 2008/0027424 A1 | 1/2008 | DeCarlo et al. |

FOREIGN PATENT DOCUMENTS

| | | |
|---|---|---|
| EP | 0171967 A | 2/1986 |
| EP | 0246350 | 11/1987 |
| EP | 0310431 | 4/1989 |
| EP | 0608609 | 8/1994 |
| EP | 1070518 A2 | 1/2001 |
| EP | 1465037 A | 10/2004 |
| EP | 1 559 377 A1 | 8/2005 |
| EP | 1645234 | 4/2006 |
| EP | 1656900 | 5/2006 |
| FR | 2864439 | 7/2005 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |
| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 9724074 | 7/1997 |
| WO | WO 99/01074 | 1/1999 |
| WO | WO 99/04710 | 2/1999 |
| WO | WO 99/22657 | 5/1999 |
| WO | WO 99/43268 | 9/1999 |
| WO | WO 00/67846 | 11/2000 |
| WO | WO 01/00114 A1 | 1/2001 |
| WO | WO 03/088858 A1 | 10/2003 |
| WO | WO 2004/045436 | 6/2004 |
| WO | WO 2005/009528 | 2/2005 |

OTHER PUBLICATIONS

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedance", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Suppl 1) :40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et al., "Image-guided Radiofrequency Tumor Ablation: Challenges and Opportunities—Part I", (2001) *J Vasc. Interv. Radiol*, vol. 12, pp. 1021-1032.

McGahan et al. (1995) "Percutaneous Ultrasound-guided Radiofrequency Electrocautery Ablation of Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

Bulletin of the American Physical Society, vol. 47, No. 5, Aug. 2002.

McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

European Search Report from Application EP 05025423.4 dated Jan. 12, 2007.

European Search Report from Application EP 06019768 dated Jan. 8, 2007.

European Search Report from Application EP 05025424 dated Jan. 23, 2007.

European Search Report from Application EP 07009028 dated Jul. 16, 2007.

European Search Report for European Application No. 09165976.3 dated Mar. 10, 2010.

\* cited by examiner

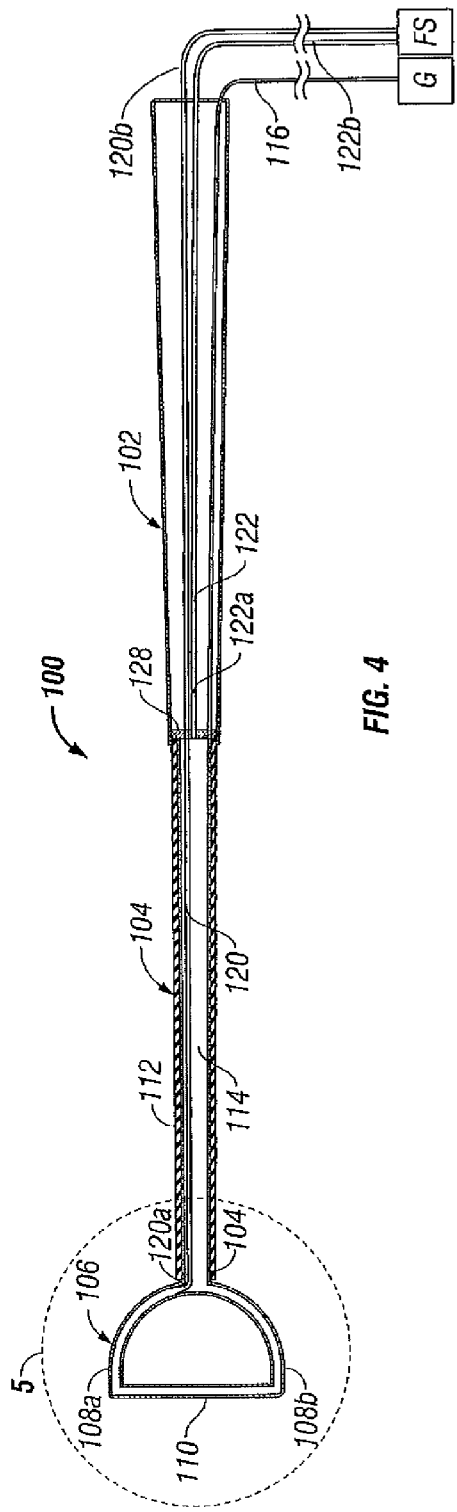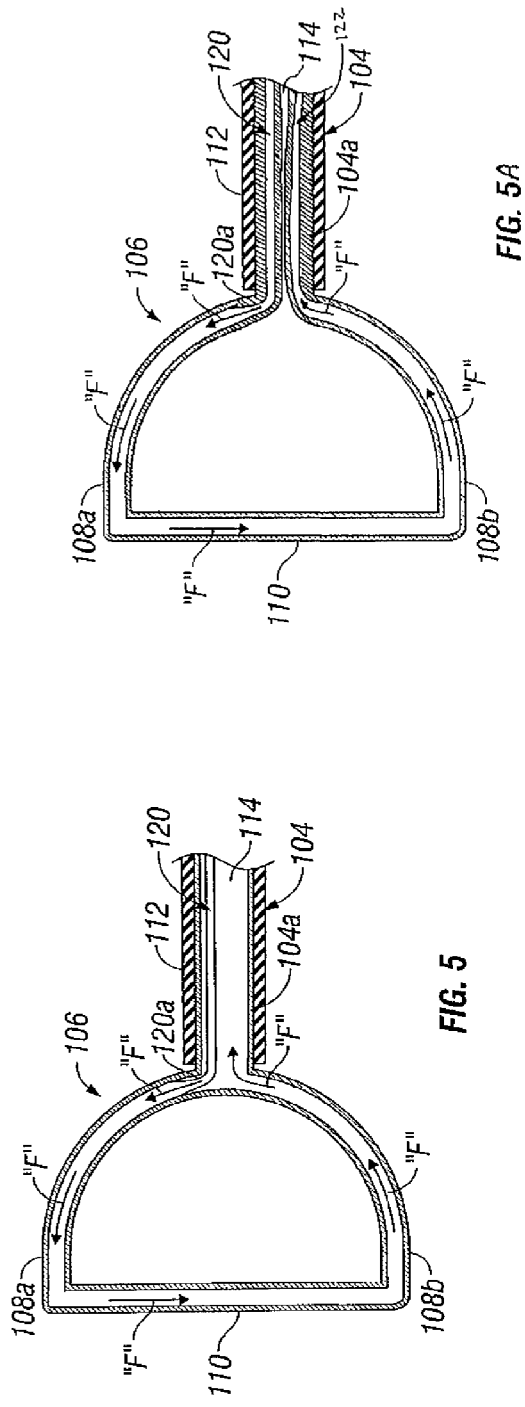
FIG. 4
FIG. 5
FIG. 5A

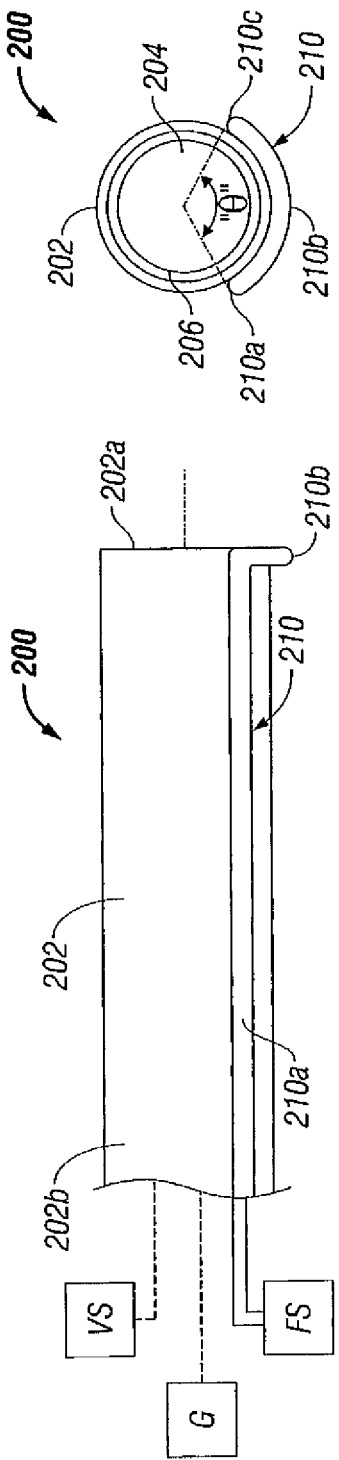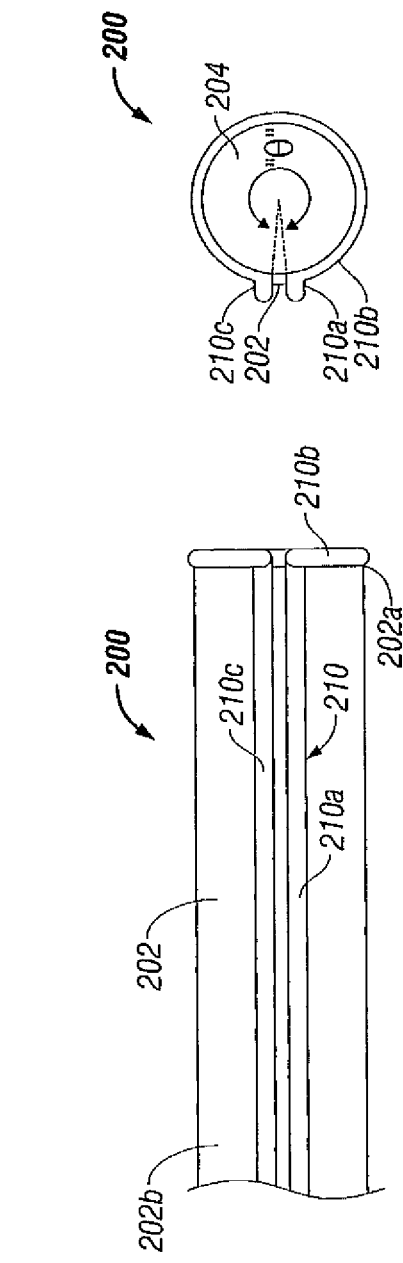

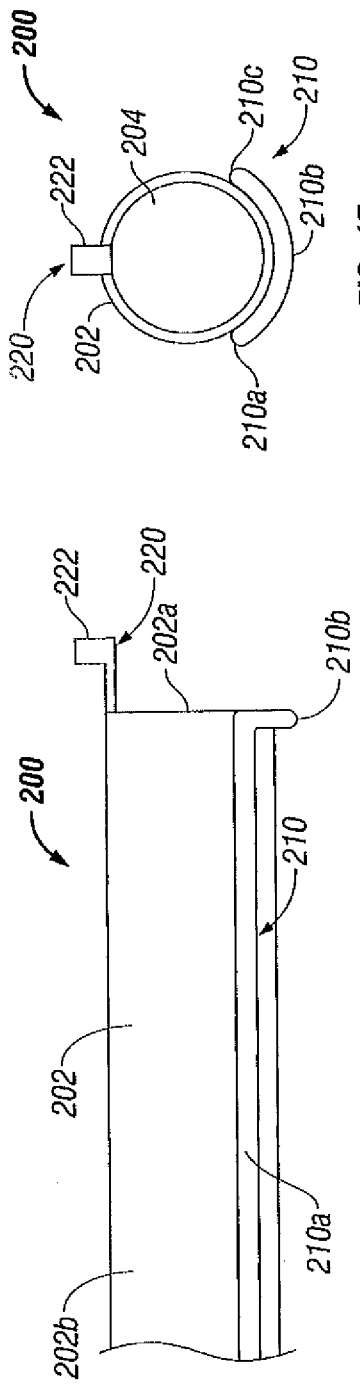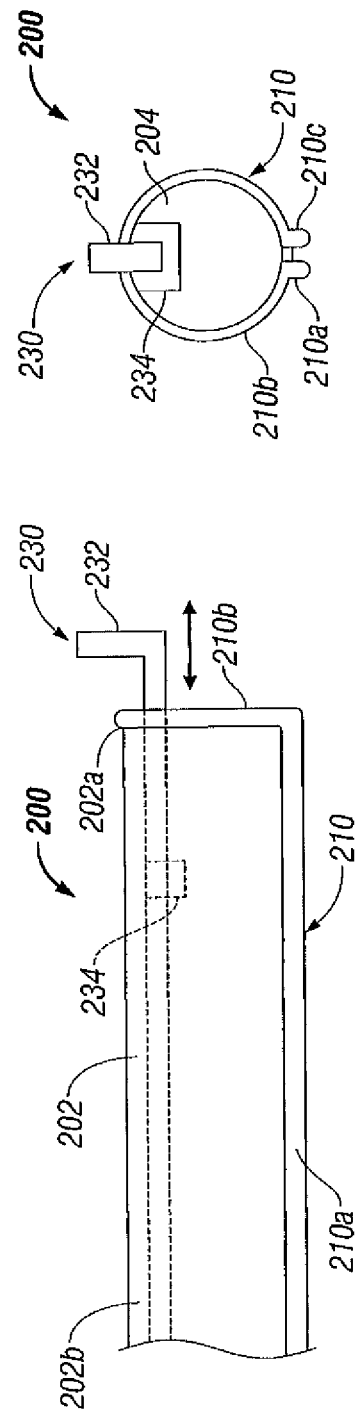

ELECTROSURGICAL DEVICES, SYSTEMS AND METHODS OF USING THE SAME

BACKGROUND

1. Technical Field

The present disclosure relates to electrosurgical devices and, more particularly, to electrosurgical devices, systems, and methods that include one or more lumens adapted to operatively connect to one or more outside sources.

2. Discussion of Related Art

Electrocauterization, commonly referred to as electrosurgery, is a commonly used medical technique whereby radiofrequency (RF) and other forms of energy are used to treat and/or to remove tissue. Tissue that is to be treated and/or to be removed may be located in a wide variety of targets within the body, including but not limited to the abdominal organs, the thoracic cavity and lymphoid tissue, including the tonsils and adenoids.

Typically, electrocauterization is performed using electrosurgical devices (e.g., suction coagulator, commercially available ValleyLab Inc., and sold as product No. E2G12-6, or other suitable electrosurgical curette), which may include an RF electrode configured to ablate, seal, desiccate and/or coagulate tissue. Generally, the desiccation and/or coagulation electrode is coupled between a power source, e.g., an electrosurgical generator, (outside the body) and a dispersive return electrode (e.g., a return electrode) or an indifferent electrode, e.g., return electrode, for contacting a large surface of the body. When an RF voltage is provided between the desiccation and/or coagulation electrode and the return electrode, RF current flows between the desiccation and/or coagulation electrode through the body and to the return electrode. Typically, the current density is very high near the tip of the desiccation and/or coagulation electrode, which heats the adjacent tissue.

An important criterion when using electrode desiccation and/or coagulation systems relates to the temperature of the electrode achieved during the desiccation and/or coagulation process. Specifically, it may be desirable to control or maintain the temperature of certain desiccation and/or coagulation electrodes, of a given electrode tip geometry, such in order to maximize coagulation. Limiting the temperature of the electrode prevents the desiccated tissue from overheating. Over heated tissue may stick to or accumulate on or near the electrode and/or the treated tissue.

Electrosurgery is frequently used today to achieve hemostasis, such as, for example, when excising, scraping, and/or sculpting tissue. Excising tissue may require a clinician to scrape and/or slice off a thin section of tissue. This may be achieved with a sharp electrosurgical curette and/or suction coagulator. Typically, after excising tissue with a sharp edge, control of hemostasis is lost, and the electrosurgical curette and/or suction coagulator is used to regain control of the ensuing bleeding. In this instance, the electrosurgical curette and/or suction coagulator may provide surface desiccation and/or coagulation to the surrounding hemorrhaging tissue. However, because current densities at or near the tip of the electrode may become very high, eschar (thermally deadened and oxidized protein) may sometimes stick to or accumulate on or near the electrode and the treated tissue. Eschar sticking or accumulating at or near the electrode may become problematic. For example, eschar sticking or accumulating at or near the electrode may cause a clinician further/continued loss control of the hemostatic effect delaying progress in a surgical procedure.

Commercially available electrosurgical curettes, such as, for example, those disclosed in U.S. Pat. No. 6,749,608 to Garito et al., include an elongated structure defining a central axis therethrough. The elongate structure includes a handle at a proximate end thereof. The elongated structure terminates in a downwardly extending claw-shaped end. Suspending from the claw-shaped end is a non-cooled cutting blade. Because the cutting blade of the electrosurgical curette of the '608 patent has a sharp blade edge and is non-cooled, there is limited ability to provide an effective hemostasis as it is cutting through tissue.

A similar electrosurgical curette is described in U.S. Pat. No. 6,802,842, to Ellman et al. The curette of the '842 patent includes a tonsil and adenoid device that includes an electrode with an electrically conductive cutting edge. While the '842 patent describes that a fluid source may be connected to the electrosurgical curette, the fluid source is not in fluid communication with the electrode. Because the cutting blade of the curette of the '842 patent is substantially sharp and non-cooled, there is limited ability to provide an effective hemostasis as it is cutting through tissue.

Accordingly, a need exists for the manufacture of electrosurgical devices for tissue desiccation and/or coagulation, systems for tissue desiccation and/or coagulation that include the electrosurgical devices and methods for desiccating and/or coagulating tissues using cooled RF desiccation and/or coagulation devices.

SUMMARY

The present disclosure provides a desiccation device configured for operation on a target tissue. The desiccation device includes a handle, and a shaft extending distally therefrom, wherein the shaft defines a lumen. Supported at a distal end of the shaft is a head having a loop configuration. The head is hollow and defines a lumen, wherein the lumen is in fluid communication with the lumen of the shaft, such that a fluid is circulatable through the lumen of the shaft and the head. In an embodiment, at least a portion of the scraping head is electrically connected to a source of electrosurgical energy.

The present disclosure also provides a desiccation device for operation on a target tissue, wherein the desiccation device includes a handle, a shaft extending distally from the handle, and a scraping head supported on a distal end of the shaft. The desiccation device includes a probe operatively supported by either the handle or the shaft. The probe includes an in-flow tube, an out-flow tube concentrically disposed about the in-flow tube and a loop supported at a distal end of the out-flow tube.

In embodiments, the loop may be hollow and may be disposed in fluid communication with the in-flow tub and the out-flow tube. A fluid circulates through the loop by way of the in-flow tube and the out-flow tube. A source of electrosurgical energy may be connected to the electrosurgical device. In embodiments, the loop of the probe may be connected to a source of electrosurgical energy.

Additionally, the present disclosure provides a surgical device for operation on a target tissue. The device may include a tubular body portion defining a lumen therethrough and a hollow electrode operatively associated with the tubular body. The electrode may include a first portion and a third portion each extending along a length of the tubular body. Each of the first and third portions of the electrode may be fluidly connected to a fluid source. The electrode also may include a second portion that extends radially around a portion of the periphery of the tubular aspiration body. The interior of the aspiration body may be selectively coated to prevent electrosurgical current from further desiccation of aspirated tissue.

Moreover, the present disclosure provides a surgical device for operation on a target tissue. The device includes a shaft that defines a longitudinal axis, supports a suction lumen and is adapted to connect to a fluid source. Operatively connected to a distal end of the shaft is an electrode that includes a scraping edge. In embodiments, a portion of the electrode is disposed in a fixed spaced apart relation relative to the suction lumen such that the suction lumen may aspirate coagulated tissue.

BRIEF DESCRIPTION OF THE DRAWINGS

Further features and advantages of the invention will become readily apparent from the following specification and from the drawings, in which:

FIG. 4 is a schematic illustration of a desiccation system, including the desiccation device of FIGS. 1-3 shown in cross-section;

FIG. 5 is an enlarged view of the indicated area of detail of FIG. 4;

FIG. 5A is an enlarged view of the indicated area of detail "5" of FIG. 4, illustrating an alternate embodiment of the present disclosure;

FIG. 12 is a side, elevational view of a distal end of a surgical device according to an embodiment of the present disclosure;

FIG. 13 is a front, elevational view of the surgical device of FIG. 12;

FIG. 14 is a side, elevational view of a distal end of a surgical device according to another embodiment of the present disclosure;

FIG. 15 is a front, elevational view of the surgical device of FIG. 14;

FIG. 16 is a side, elevational view of a distal end of a surgical device according to yet another embodiment of the present disclosure;

FIG. 17 is a front, elevational view of the surgical device of FIG. 16;

FIG. 18 is a side, elevational view of a distal end of a surgical device according to still another embodiment of the present disclosure;

FIG. 19 is a front, elevational view of the surgical device of FIG. 18;

DETAILED DESCRIPTION OF EMBODIMENTS

Figure 1:
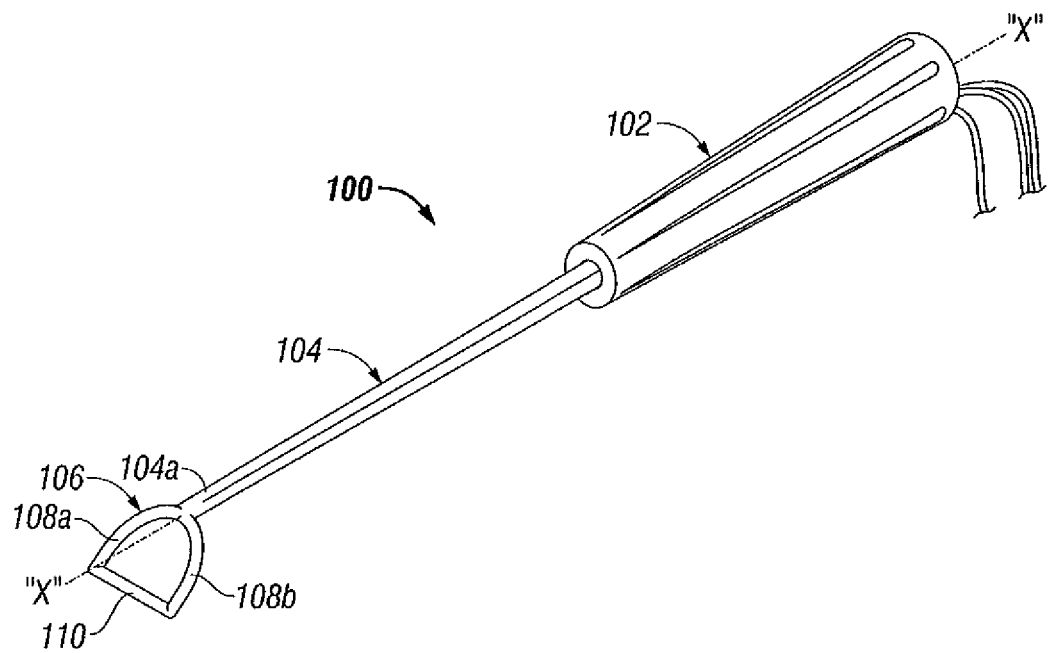
FIG. 1 is an isometric perspective view of a desiccation device according to an embodiment of the present disclosure.

In the drawings and in the descriptions which follow, the term "proximal", as is traditional, will refer to the end which is closer to the user, while the term "distal" will refer to the end which is further from the user.

For illustrative purposes only, the electrosurgical devices described herein, will be described in terms of electrosurgical systems that include RF desiccation and/or coagulation modes. As mentioned above, the present disclosure relates to electrosurgical devices that employ RF desiccation and/or coagulation electrodes. The electrosurgical devices, as described herein, may be configured to operate in different modes of operation, e.g., ablate, desiccate, coagulate, and/or seal. Additionally, the electrosurgical devices, as described herein, may be adapted to connect to one or more different sources (e.g., electrosurgical generator) for producing a desired effect.

Referring now to the figures, in which like numerals indicate like parts, and particularly to FIG. 1, desiccation device according to an embodiment of the present disclosure is shown generally as 100. As seen in FIG. 1, desiccation device 100 includes a handle 102, a shaft 104 extending coaxially from handle 102, and a head 106 supported on or formed at a distal end 104a of shaft 104. Handle 102 and shaft 104 may be substantially aligned along a common longitudinal "X" axis thereof or, in the alternative, may be parallel to one another and off-axis or may be angled with respect to one another.

Figure 2:
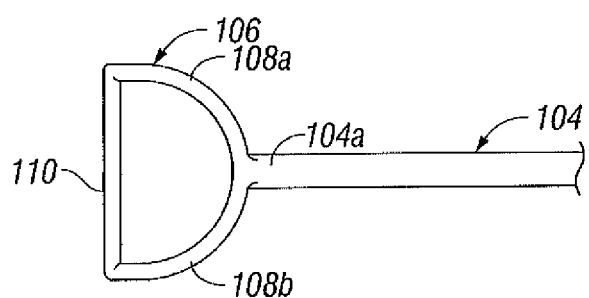
FIG. 2 is a top, plan view of the desiccation device of FIG. 1.
Figure 3:
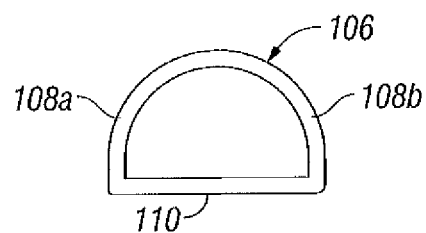
FIG. 3 is a front elevational view of the desiccation device of FIGS. 1 and 2.

The specific configuration of head 106 may best be seen with reference to FIGS. 2 and 3. As shown therein, head 106 is in the form of a loop. In an embodiment, head 106 may include a pair of diverging arms 108a, 108b and a cross-bar 110 extending between the distal ends of arms 108a, 108b. Cross-bar 110 may or may not be sharpened as needed to achieve the correct speed of cutting balanced against the level of desiccation coagulation. Arms 108a, 108b of head 106 extend in a direction that is generally transverse to the longitudinal "X" axis.

Handle 102, shaft 104 and head 106 may be formed as a unitary construction of a suitably electrically conductive material. It is contemplated that at least a portion of each of handle 102, shaft 104 and head 106 may be covered with a suitably electrically insulative material or the like. In an embodiment, as best seen in FIGS. 4 and 5, desiccation device 100 includes a handle 102 constructed of a suitable electrically insulative material, and a shaft 104 and head 106 fabricated from a suitable electrically conductive material, such as, for example, stainless steel, titanium, etc. As seen in FIGS. 4 and 5, at least a portion of the length of shaft 104 is covered with a suitable electrically insulative material 112. It is envisioned that insulative material 112 may extend to cover at least a portion of arms 108a, 108b of head 106 thereby solely exposing cross-bar 110 as an active electrosurgical electrode.

As seen in FIG. 4, shaft 104 and head 106 are electrically connected to a source of electrosurgical energy or generator "G" via a conduit 116 (e.g., wire, cable, etc.). A suitable generator "G" should be capable of delivering at least one energy frequency ranging from about 100 kilohertz to about several hundred megahertz.

With continued reference to FIGS. 4 and 5, shaft 104 and head 106 are hollow and define a lumen 114 therein and/or therethrough. Desiccation device 100 includes an in-flow tube 120 disposed within lumen 114. In-flow tube 120 includes a distal end 120a that is in close proximity to the portion of lumen 114 defined by head 106. As seen in FIGS. 4 and 5, distal end 120a of in-flow tube 120 may extend into the portion of lumen 114 defined by head 106. A fluid-tight seal may be created, at a point where in-flow tube 120 extends into a portion of lumen 114 defined by head 106, by joining distal end 120a, or portions thereof, to lumen 114. In this instance, cooling fluid is prevented from flowing back into the portion of lumen 114 defined by head 106 before entering distal end 122a of out-flow tube 122. This configuration may provide a maximum cooling effect to head 106. In-flow tube 120 includes a proximal end 120b extending through handle 102 which fluidly connects or is connectable to a source of fluid "FS".

As seen in FIG. 4, desiccation device 100 includes an out-flow tube 122 having a distal end 122a in fluid communication with lumen 114 of shaft 102, and a proximal end 122b extending from handle 102 which fluidly connects or is connectable to fluid source "FS".

Desiccation device 100 includes one or more hubs 128 (see FIG. 4) supported within handle 102. Hub 128 functions to create one or more fluid-tight seals for lumen 114 between lumen 114 and in-flow tube 120 and out-flow tube 122.

The components of desiccation device 100 are not drawn to scale. Accordingly, it is envisioned that the relative sizes of the components may vary depending on the intended purpose. For example, it is contemplated that a diameter of in-flow tube 120 may be selected to maximize fluid deliver and that the diameter thereof may taper, in a distal direction, so as to form head 106. It is further contemplated that a cross-sectional diameter of the tube making up head 106 may be shaped or sized to balance the desiccating, cutting and/or debriding effect of head 106. It is further contemplated that cross-bar 110 of head 106 may have a round, transverse cross-sectional profile and/or that a diameter of cross-bar 110 of head 106 may be smaller than a diameter of in-flow tube 120.

In operation, either prior to, during or after activation of generator "G", as electrosurgical energy is delivered to head 106, a cooling fluid "F" (e.g., water, saline, etc.) is circulated through lumen 114. Fluid "F" is fed, from the source of fluid "FS", through in-flow tube 120 to the portion of lumen 114 defined by head 106, circulated around that portion of lumen 114, back through lumen 114 extending through shaft 104, and out through out-flow tube 120 and back to the fluid source "FS".

In an embodiment, as seen in FIG. 5A, it is contemplated that out-flow tube 122 may extend distally to and fluidly connect with arm 108b of head 106. As such, it is envisioned that a single unitary tube may be used to form in-flow tube 120, head 106 and out-flow tube 122.

It is further contemplated that a distal end of in-flow tube 120 and/or out-flow tube 122 (not shown), e.g., distal of hub 128, may be disposed in a support tube or respective support tubes (not shown) or the like.

Circulation of fluid "F", as described above, may be established with a pump (not shown). The rate of circulation of fluid "F" may be increased or decreased in order to adjust the temperature of head 106 as needed. A probe (not shown) may be connected to head 106 which may sense the temperature of head 106 during the surgical procedure. The probe may be connected to generator "G" and/or the fluid source "FS" in order to provide generator "G" and/or the fluid source "FS" with feedback and thus enable generator "G" and/or the fluid source "FS" to be adjusted as needed and/or desired.

In operation, with head 106 activated and fluid "F" circulating therethrough, head 106 is advanced through to desiccate tissue without substantial production of eschar or the like. The desiccated tissue may then be excised (e.g., cut) as desired and/or needed.

Turning now to FIGS. 6-8B, a desiccation device according to an alternate embodiment of the present disclosure is shown and described. The desiccation device of FIGS. 6-8B is substantially similar to the desiccation device of FIGS. 1-5 and thus will only be described herein to the extent necessary to identify differences in construction and/or operation.

As seen in FIGS. 6-8B, desiccation device 100 may include either a hollow or solid shaft 104 and/or head 106. Shaft 104 and/or head 106 may be fabricated from a suitable electrically conductive material, a suitable electrically insulative material, or a combination thereof. It is envisioned that cross-bar 110 of head 106 may define a knife edge or the like for severing and/or cutting though tissue before, during or after desiccation of said tissue.

Figure 8A:
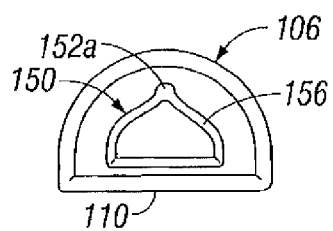
FIG. 8A is a front elevational view of the desiccation device of FIGS. 6 and 7.
Figure 8B:
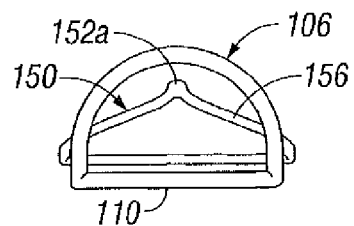
FIG. 8B is a front elevational view of an alternate embodiment of the desiccation device of FIG. 8A.

With continued reference to FIGS. 6-8B, desiccation device 100 includes a probe 150 operatively connected to handle 102 and/or shaft 104. As best seen in FIGS. 8A and 8B, probe 150 may have a width that is less than head 106 (FIG. 8A), or greater than cutting head 106 (FIG. 8B). Probe 150 includes an outer or out-flow tube 152 and a concentric inner or in-flow tube 154. Probe 150 further includes a loop 156 formed or supported at a distal end 152a of out-flow tube 152. Loop 156 may be hollow in order to allow fluid "F" to circulate therethrough. It is envisioned that a distal end of in-flow tube 154 is located in close proximity to the hollow cavity of loop 156. In this manner, fluid "F" may be delivered to and circulated around loop 156 by in-flow tube 154 and carried away by out-flow tube 152.

As seen in FIGS. 6-8B, loop 156 is located proximally of head 106. In this manner, as desiccation device 100 is moved in a proximal direction, as indicated by arrow "A", loop 156 is maintained ahead of head 106 to thereby desiccate the target tissue prior to the cutting of the target tissue by cross-bar 110 (e.g., a cutting knife of blade).

Figure 6:
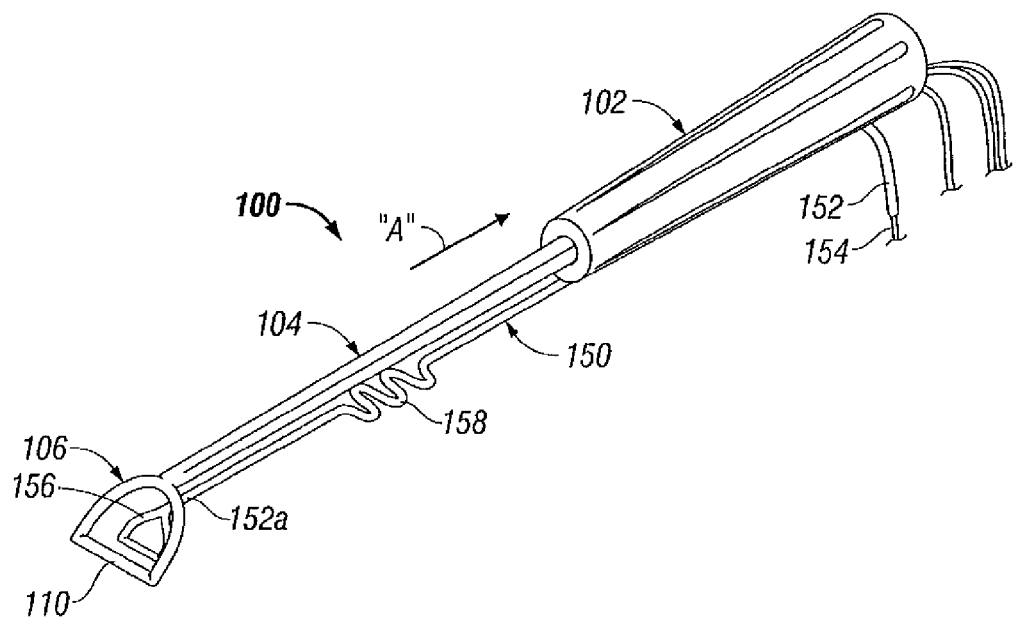
FIG. 6 is an isometric perspective view of a desiccation device according to another embodiment of the present disclosure.
Figure 7:
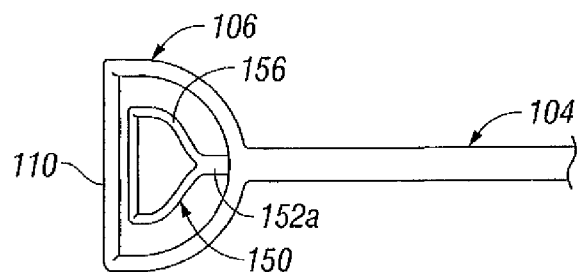
FIG. 7 is a top, plan view of the desiccation device of FIG. 6.

In one embodiment as seen in FIG. 6, probe 150 may include one or more spring elements 158 formed in out-flow tube 152 and in-flow tube 154 that are concentric with one another. Spring elements 158 provide probe 150 with a degree of resiliency during its movement over and against the target tissue.

Figure 9:
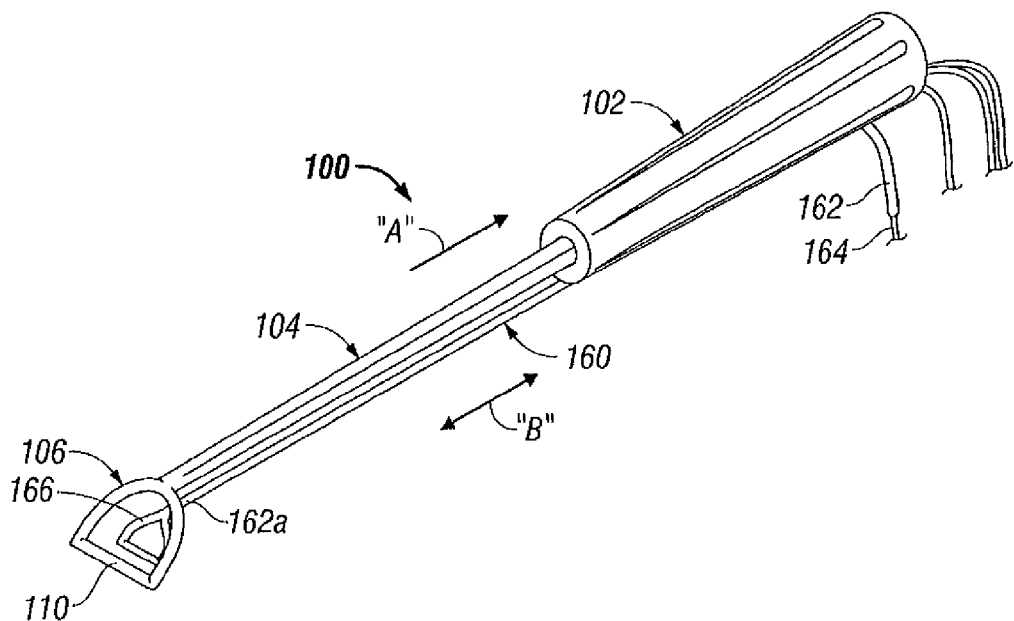
FIG. 9 is a side, elevational view of a desiccation device according to yet another embodiment of the present disclosure.
Figure 10:
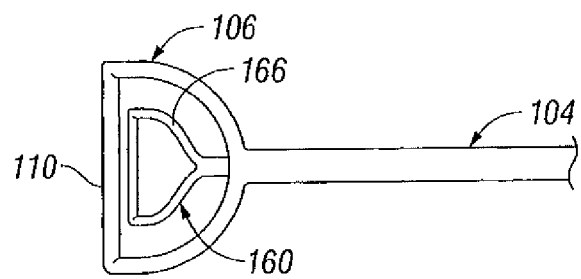
FIG. 10 is a top, plan view of the desiccation device of FIG. 9.
Figure 11:
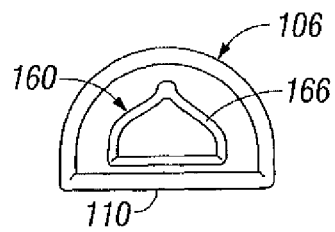
FIG. 11 is a front elevational view of the desiccation device of FIGS. 8 and 9.

Turning now to FIGS. 9-11, a desiccation device according to an alternate embodiment of the present disclosure is shown and described. The desiccation device of FIGS. 9-11 is substantially similar to the desiccation device of FIGS. 6-8 and thus will only be described herein to the extent necessary to identify differences in construction and/or operation.

As seen in FIGS. 9-11, desiccation device 100 includes a probe 160 operatively and slidably connected to handle 102 and/or shaft 104. Probe 160 includes an outer or out-flow tube 162 and a concentric inner or in-flow tube 164. Probe 160 further includes a loop 166 formed or supported at a distal end 162a of out-flow tube 162. Loop 166 may be hollow in order to allow fluid "F" to circulate therethrough. It is envisioned that a distal end of in-flow tube 164 is located in close proximity to the hollow cavity of loop 166. In this manner, fluid "F" may be delivered to and circulated around loop 166 by in-flow tube 164 and carried away by out-flow tube 162.

As seen in FIGS. 9-11, loop 166 may be located proximally of cutting head 106. In this manner, as desiccation device 100 is moved in a proximal direction, as indicated by arrow "A", loop 166 is maintained ahead of cutting head 106 to thereby desiccate the target tissue prior to the cutting of the target tissue by cutting knife 110. Additionally, since probe 160 is slidably connected to handle 102 and/or shaft 104, probe 160 may be moved relative thereto such that loop 166 may be positioned distal of, or in juxtaposition to, cutting head 106. The movement of probe 160 relative to handle 102, shaft 104 and/or cutting head 106 is indicated by double-headed arrow "B".

It is contemplated that in an embodiment, desiccation device 100, of FIGS. 9-11, may be configured as a bipolar device wherein head 106 may be either an active or a return portion of a bipolar arrangement and loop 166 may be the other of the active or return portion of the bipolar arrangement. In such an embodiment, it is further contemplated that each of head 106 and loop 166 may be provided with a common or an independent fluid circulating therethrough in order to provide a cooling effect thereto.

Turning now to FIGS. 12 and 13, a surgical device according to another embodiment of the present disclosure is shown generally as 200. As seen in FIGS. 12 and 13, desiccation device 200 includes a body portion 202 having a substantially tubular configuration and defining a lumen 204 therein. Body portion 202 further defines a longitudinal "X" axis.

Surgical device 200 further includes an electrode 210 operatively associated with body portion 202. Electrode 210 includes a first portion 210a which extends longitudinally along an outer surface of body portion 202 towards a distal end 202a thereof, a second portion 210b which extends around at least a portion of the periphery of body portion 202, and a third portion 210c which extends longitudinally along the outer surface of body portion 202 towards a proximal end 202b thereof.

As seen in FIGS. 12 and 13, second portion 210b of electrode 210 is located adjacent body portion 202. Additionally, second portion 210b extends around the periphery of body portion 202 by an angle "θ" which is less than about 180°, preferably, about 60°.

Body portion 202 may be fabricated from any suitable rigid material, including and not limited to, stainless steel, titanium, polycarbonate, polyvinylchloride and the like. Electrode 210 is fabricated from any suitable electrically conductive material, including and not limited to stainless steel, titanium and the like. It is envisioned that at least first portion 210a and third portion 210c of electrode 210 is covered with a suitable insulative material thereby leaving second portion 210b thereof exposed.

Electrode 210 may be hollow thereby defining a circulation path for fluid to flow therethrough. It is envisioned that a proximal end of first portion 210a and second portion 210b of electrode 210 are each fluidly connected or connectable to fluid source "FS". It is further envisioned that electrode 210 is electrically connected or connectable to an electrosurgical generator "G". Body portion 202 of surgical device 200 may be connected to a vacuum source "VS" for creating a suction through lumen 204 thereof.

In operation, with fluid circulating through electrode 210 and with electrode 210 activated, the distal end of surgical device 200 may be approximated toward a target tissue such that second portion 210b may be contacted with the target tissue and thereby desiccate the same. As the target tissue is desiccated and/or debrided, any smoke and/or loose tissue generated as a result thereof may be aspirated into body portion 202. A selective coating 206 inside shaft 202 may be employed to prevent RF flow through aspirated tissue reducing occlusion of lumen 204 by tissue chard to the inside surface.

Turning now to FIGS. 14 and 15, according to another embodiment of surgical device 200, second portion 210b of electrode 210 may extend around the distal end 202a of the periphery of body portion 202 by an angle "θ" which is greater than about 180°, preferably, about 360°. As seen in FIG. 14, second portion 210b of electrode 210 is located distal of distal end 202a of body portion 202.

Turning now to FIGS. 16 and 17, according to another embodiment of the present disclosure, surgical device 200 of FIGS. 12 and 13 further includes a scraper 220 extending distally from distal end 202a of body portion 202. Scraper 220 includes a finger 222 extending radially outward from body portion 202 which functions to rake desiccated tissue in a proximal direction or push desiccated tissue in a distal direction.

Turning now to FIGS. 18 and 19, according to another embodiment of the present disclosure, surgical device 200 of FIGS. 14 and 15 further includes a scraper 230 slidably disposed within lumen 204 of body portion 202 and extending distally therefrom. Scraper 230 includes a finger 232 extending radially outward from body portion 202 which functions to rake desiccated tissue in a proximal direction or push desiccated tissue in a distal direction. A retainer 234 is provided within lumen 204 of body portion 202 to support scraper 230.

While first and third portions 210a, 210c, respectively, of electrode 210 is shown disposed externally of body portion 202, it is envisioned and within the scope of the present disclosure for first and third portions 210a, 210c, respectively, to be disposed within lumen 204 of body portion 202.

As seen throughout FIGS. 12-19, second portion 210b of electrode 210 is oriented substantially orthogonal to the longitudinal "X" axis and to the longitudinal axis of first and/or second portions 210a, 210c thereof. However, it is envisioned that second portion 210b may be oriented at any angle with respect to the longitudinal "X" axis.

Figure 20:
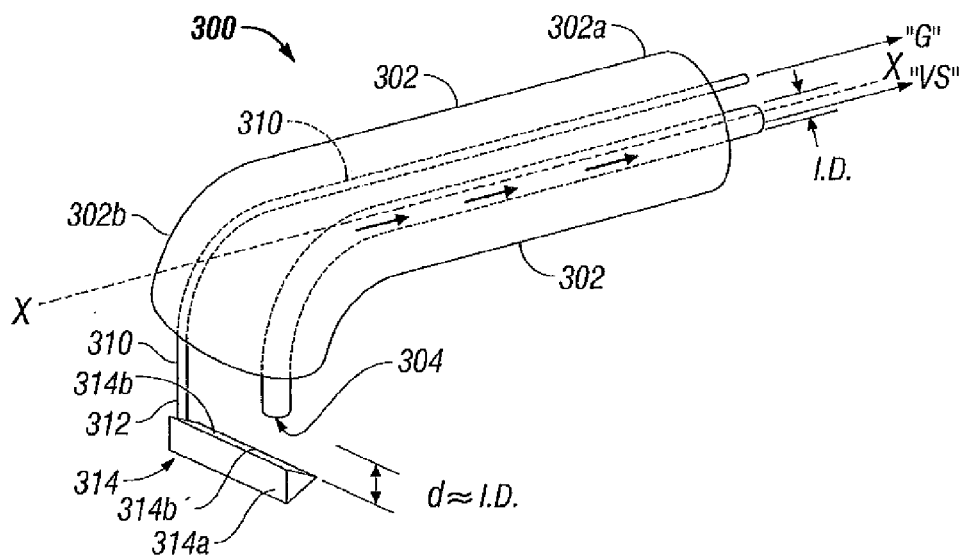
FIG. 20 is a perspective view of a surgical device according to another embodiment of the present disclosure.
Figure 21A:
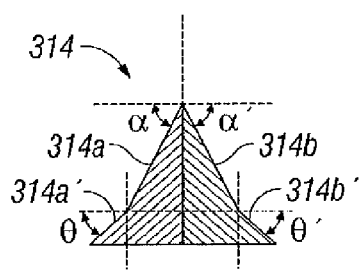
FIGS. 21A-21D are traverse, cross-sectional views illustrating different shapes of electrode assemblies, in accordance with the present disclosure, that may be employed with the surgical device depicted in FIG. 20.
Figure 21B:
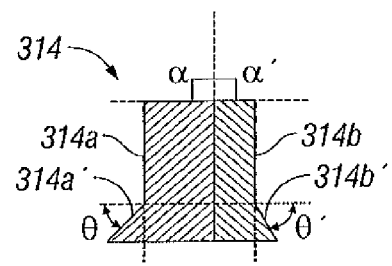
Figure 21C:
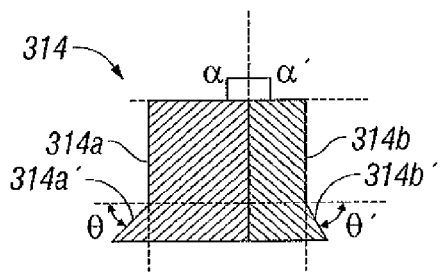
Figure 21D:
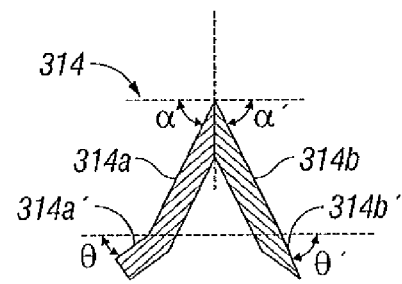
Figure 22:
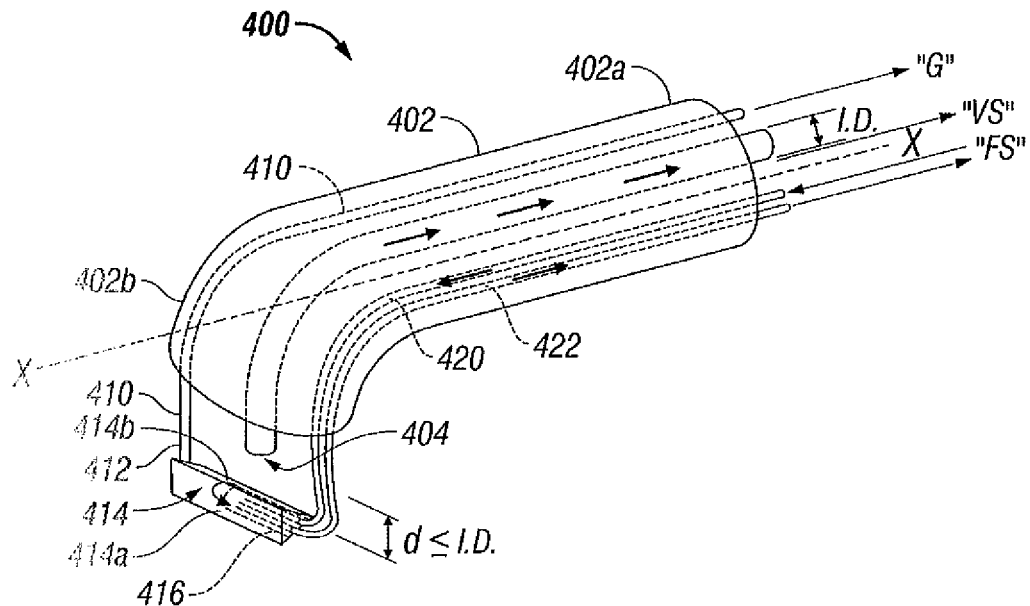
FIG. 22 is a perspective view of a surgical device according to another embodiment of the present disclosure.

Turning now to FIGS. 20-22, a surgical device 300 is shown. Surgical device 300 is substantially similar to the surgical devices described hereinabove and thus will only be described herein to the extent necessary to identify differences in construction and/or operation thereof.

Surgical device 300 includes a shaft 302 having an electrode 310 supported on, formed at or extending from a distal end 302b thereof and a suction lumen 304 operatively connected thereto and extending from a proximal end 302a to distal end 302b of shaft 302. A selective coating may be applied to the inside of shaft 304 to reduce clogging. Surgical device 300 is adapted to operatively connect to a generator "G" and a vacuum source "VS". A surgical device 400 may also be adapted to operatively connect to a fluid source "FS", to be described in greater detail below.

Shaft 302 may have a generally tubular structure defining a longitudinal axis "X" therethrough. Shaft 302 may be configured to serve as a handle for grasping thereof, or shaft 302 may be adapted to attach to a handle, not shown. Shaft 302 includes proximal end 302a and distal end 302b. Proximal end 302a of shaft 302a may be adapted to connect to generator "G", vacuum source "VS" and/or fluid source "FS". Shaft 302 may have a sheathing or insulative coating (not shown) extending over at least a portion of a length thereof, or at least a portion of shaft 302 may be made from a suitable non-conductive material.

Surgical device 300 includes a suction lumen 304 extending from or selectively extending from distal end 302b of shaft.

Suction lumen 304 may be oriented substantially orthogonal to the longitudinal "X" axis. Alternatively, suction lumen 304 may be oriented at any suitable angle θ with respect to the longitudinal "X" axis, as best seen in FIG. 20. Suction lumen 304 may be constructed of a suitable non-conductive material, or may have a suitable insulating material covering at least a portion thereof.

In one embodiment, suction lumen 304 may be a separate member attached to shaft 302 via any suitable attaching means. Alternatively, suction lumen 304 may be defined by shaft 302 or portion thereof.

As mentioned above, surgical device 300 includes an electrode 310 located at distal end 302b of shaft 302 and selectively extendable therefrom. Electrode 310 may include one or more arms 312 (one arm is shown) that extends therefrom in a generally transverse orientation relative to an axis thereof. Each arm 312 may be formed of a suitable electrically conductive material that may be at least partially coated with a suitable insulative material. Alternatively, each arm 312 may include an inner conductor surface and an outer non-conductive sheath (not shown). Surgical device 300 includes one or more fingers 314 (one finger is shown) extending from arm 312.

When viewing at surgical device 300 from the front, finger 314 and arm 312 of electrode 310 appear generally "L" shaped.

Finger 314 may extend from arm 312 in any suitable direction. Finger 314 may have a variety of different geometric shapes and/or configurations to include a leading conductive distal edge 314a and a trailing non-conductive proximal edge 314b'. As seen in FIGS. 21A-21D, finger 314 may have a transverse cross-sectional profile that resembles a square, triangular, rectangle, trapezoid, and the like, or finger 314 may have an irregular "free-form" shape (e.g., teepee, carrot).

Finger 314 may include a conductive surface 314a in electrical communication with the generator "G", and a non-conductive surface 314b isolated from conductive surface 314a. Conductive surface 314a may extend distally from an intermediate plane of finger 314 at an angle α that is between about 0° and 90° (FIGS. 21A-21D) forming conductive distal edge 314a' projecting distally from conductive surface 314a. Non-conductive surface 314b of finger 314 may extend proximally from the intermediate plane of finger 314 at an angle α' that is between about 0° and 90° (FIGS. 21A-21D) forming non-conductive proximal scraping edge 314b' extending from non-conductive surface 314b. Additionally, conductive distal edge 314a' of conductive surface 314a and scraping edge 314b' of non-conductive surface 314b may be oriented at any angle θ relative to a distal end 304a of suction lumen 304 to provide more or less aggressive scraping depending on a particular purpose. For example, conductive distal edge 314a' and scraping edge 314b' may be oriented at an angle θ and θ', respectively, that is between about 0° and 90° relative to the distal end 304a suction lumen 304, as best seen in FIGS. 21A-21D).

Distal edge 314a' may be configured to have a generally dull edge. In an embodiment, edge 314a' and a proximal scraping edge 314b' of finger 314 may each be angled or straight.

Scraping edge 314b' may be formed of non-conductive material, such as, for example, ceramic or high temperature plastic, e.g., liquid crystal polymer. Alternatively, scraping edge 314b', or any portion thereof, may be coated with an insulative material. Scraping edge 314b' may be configured to have a minimal sharpness. That is, proximal edge 314b' should be sharp enough to scrape or slough tissue that has been coagulated, and pass over tissue that has not been coagulated.

Scraping edge 314b' may be in a fixed spaced apart relation relative to suction lumen 304. In particular, scraping edge 314b' is spaced apart from suction lumen 304 at a distance "d" such that suction lumen 304 may aspirate coagulated and/or desiccated tissue and aspirate fluids in the proximity of tissue being treated. As seen in FIGS. 20 and 22, distances "d" that scraping edge 314b' may be disposed from suction lumen 304 include, and are not limited to, distances that are approximately less than or equal to the inner diameter (I.D.) of suction lumen 304.

For example, as seen in FIG. 20, for suction lumens 304 with an I.D. of 12 French or less, scraping edge 314b' may be spaced apart from suction lumen 304 by a distance "d" that is approximately equal to the I.D. of suction lumen 304. For suction lumens 304 with an I.D. that is greater than 12 French, as seen in FIG. 22, scraping edge 314b' may be spaced apart from suction lumen 304 by a distance "d" that is approximately less than the I.D. of suction lumen 304. As used herein, a "French" is approximately equal to a diameter of the lumen times 3 mm.

The following steps are illustrative of one mode in which surgical apparatus 300 may be employed. In operation, with distal edge 314a' of electrode 310 activated, distal edge 314a' is advanced over a desired tissue to coagulate and/or desiccate the tissue. Subsequently, a layer of the coagulated and/or desiccated tissue may be scraped off via the scraping edge 314b' of electrode 310 and aspirated by suction lumen 304. If additional layers of tissue have to be removed, they may be removed employing the same or similar steps as herein described.

Turning now to FIG. 22, a surgical device 400 is shown. Surgical device 400 is substantially similar to surgical device 300 described hereinabove and thus will only be described herein to the extent necessary to identify differences in construction and/or operation thereof.

Surgical device 400 includes a shaft 402 having an electrode 410 supported on or formed at a distal end 402b thereof and a suction lumen 404 operatively connected thereto and extending from a proximal end 402a to distal end 402b.

Surgical device 400 further includes an inflow conduit 420 and an outflow conduit 422 each operatively fluid interfacing electrode 410 with a fluid source "FS". In an embodiment, inflow conduit 420 and outflow conduit 422 may be defined by shaft 402 and may extend along a longitudinal length thereof.

While electrode 410 is illustrated as having the same or similar configuration to electrode 310, electrode 410 may have a loop configuration the same as or similar to the loop configuration described with reference to cutting head 106. Electrode 410 is hollow and defines a lumen 416 in fluid communication with inflow conduit 420 and outflow conduit 422 of shaft 402. In use, a fluid is circulatable through inflow conduit 420 and outflow conduit 422 of shaft 402 to cool electrode 410.

Inflow conduit 422 and outflow conduit 422 of shaft 402 may be configured the same as or similarly to in-flow tube 120 and out-flow tube 122 as described hereinabove.

The following steps are illustrative of one mode in which surgical apparatus 400 may be employed. In operation, with distal edge 414a' of electrode 410 activated, distal edge 414a' is advanced over a desired tissue to coagulate and/or desiccate the tissue. Subsequently, a layer of the coagulated and/or desiccated tissue may be scraped off via the scraping edge 414b' of electrode 410 and aspirated by suction lumen 404. As mentioned above, if additional layers of tissue have to be removed, they may be removed employing the same or similar steps as herein described. However, if numerous advancements of electrode 410 over tissue are made, electrode 410 and/or any portion thereof may become too hot, and for at least the same or similar reasons stated above, it may be useful to circulate fluid into electrode 410 or a portion thereof, via inflow and outflow conduits, 420 and 422, respectively, to cool electrode 410.

From the foregoing and with reference to the various figure drawings, those skilled in the art will appreciate that certain modifications can also be made to the present disclosure without departing from the scope of the same. For example, surgical devices 300 and 400 may include a sensor, not shown, operatively connected thereto and in operative communication with suction lumens 304 and 404 and/or electrodes 310 and 410. The sensor may be configured to detect the direction that surgical devices 300 and 400 are moving. The sensor may also be configured to detect pressure changes at electrodes 310 and 410. The sensor may be configured as part of a temperature control circuit in conjunction with the fluid source.

Figure 23:
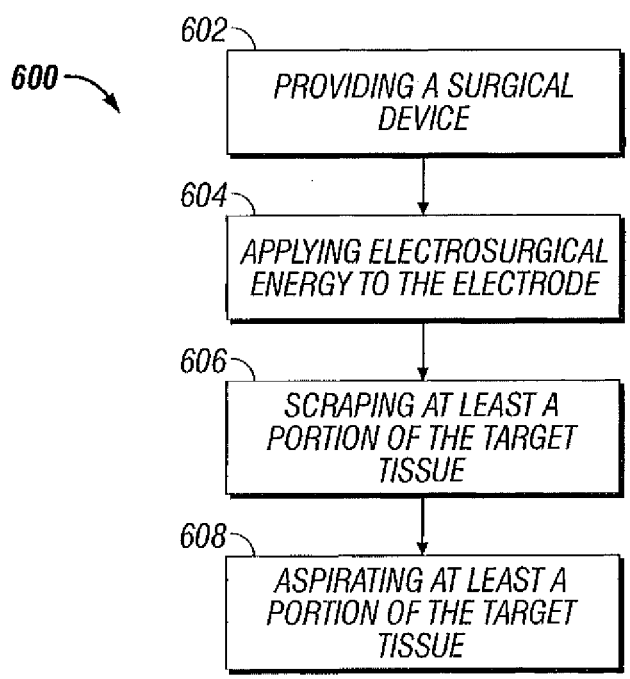
FIG. 23 is a flow chart illustrating a method, in accordance with the present disclosure, for performing a surgical procedure.

With reference to FIG. 23 there is shown a flow chart 600 illustrating a method for performing a surgical procedure. According to an exemplary method of operation, illustrated at step 602, a surgical device, for operation on a target tissue, is provided. The device includes a shaft, the shaft defining a longitudinal axis therethrough and a suction lumen. The shaft adapted to connect to at least one outside source. The device also includes an electrode operatively connected to the shaft and supported at a distal end thereof. The electrode includes a scraping edge. At least a portion of the electrode is disposed in a fixed spaced apart relation relative to the suction lumen such that lumen may aspirate coagulated tissue. Illustrated at step 604, electrosurgical energy to the electrode, for achieving a desired tissue effect to a target tissue, is applied. Illustrated at step 606, at least a portion of the target tissue is scraped. Illustrated at step 608, at least a portion of the target tissue is aspirated.

Although the subject devices, systems and methods have been described with respect to preferred embodiments, it will be readily apparent, to those having ordinary skill in the art to which it appertains, that changes and modifications may be made thereto without departing from the spirit or scope of the subject of the present disclosure.

What is claimed is:

1. A surgical device for operation on a target tissue, the device comprising:
   a tubular body portion defining a lumen therethrough; and
   a hollow electrode extending along an outer surface of the tubular body, the electrode including a first portion extending along a length of the tubular body, a second portion extending radially along at least a portion of the periphery of the tubular body, and a third portion extending along a length of the tubular body, wherein a proximal end of each of the first and third portions of the electrode is fluidly connected to a fluid source.

2. The surgical device according to claim 1, wherein the interior of the lumen is coated to prevent clogging.

3. The surgical device according to claim 2, wherein the electrode is fabricated from an electrically conductive material, and wherein an insulative coating is disposed over at least a segment of the electrode.

4. The surgical device according to claim 3, wherein the second portion of the electrode extends by an angle of less than about 180°.

5. The surgical device according to claim 3, wherein the second portion of the electrode extends by an angle of greater than about 180°.

6. The surgical device according to claim 1, wherein the first and third portions of the electrode are covered with an insulative material.

7. The surgical device according to claim 1, wherein a vacuum source is fluidly connected to the lumen of the tubular body.

8. The surgical device according to claim 1, further comprising a scraper extending distally from the tubular body.

9. The surgical device according to claim 8, wherein the scraper is slidably supported on the tubular body and is movable relative to the tubular body.

10. The surgical device according to claim 1, wherein at least the second portion of the electrode is electrically connected to an electrosurgical energy source.

11. The surgical device according to claim 1, wherein the radial portion of the electrode has a conductive coating for further reducing char and drag on the electrode.

* * * * *